United States Patent [19]
Brisken et al.

[11] Patent Number: 5,209,235
[45] Date of Patent: May 11, 1993

[54] ULTRASONIC IMAGING CATHETER ASSEMBLY AND METHOD FOR IDENTIFICATION OF THE SAME

[75] Inventors: Axel F. Brisken, Fremont; Douglas A. LaPorte, Santa Clara, both of Calif.; Aage Gronningsaeter, Trondhjem, Norway; Michael D. Rold, Cupertino, Calif.

[73] Assignee: Cardiovascular Imaging Systems, Inc., Sunnyvale, Calif.

[21] Appl. No.: 758,879

[22] Filed: Sep. 13, 1991

[51] Int. Cl.⁵ .............................................. A61B 8/12
[52] U.S. Cl. ................................................... 128/662
[58] Field of Search ........... 128/630, 642, 675, 660.01, 128/662.06, 713, 908, 24 A

[56] References Cited

U.S. PATENT DOCUMENTS

| | | | |
|---|---|---|---|
| 4,407,298 | 10/1983 | Lentz et al. | 128/713 |
| 4,446,715 | 5/1984 | Bailey | 128/675 X |
| 4,700,708 | 10/1987 | New, Jr. et al. | 128/633 |
| 4,768,496 | 9/1988 | Kreizman et al. | 128/24 AA |
| 4,771,774 | 9/1988 | Simpson | 604/22 X |
| 4,794,931 | 1/1989 | Yock | 128/662.06 |
| 4,811,740 | 3/1989 | Ikeda et al. | 128/660.01 |
| 4,853,772 | 8/1989 | Kikuchi | 128/908 X |
| 5,000,185 | 3/1991 | Yock | 128/662.06 |

OTHER PUBLICATIONS

Lancee, C. T. et al, "Construction of a Circular Ultrasonic Array with Miniature Elements for Cardiac Application" Conference: Proceedings of 2nd European Congress on UTS in Medicine, Munich 12–16 May 1975 pp. 49–53.

*Primary Examiner*—Francis Jaworski
*Attorney, Agent, or Firm*—Townsend and Townsend Khourie and Crew

[57] ABSTRACT

An improved ultrasonic imaging catheter assembly (4) includes an elongate tubular assembly (8) having an imaging assembly (12) at one end (14) and one or more connectors (16) at the other end (17). The catheter assembly includes a digital identification circuit (26), used to permit the automatic identification of the catheter assembly, having a common ID terminal (32) and at least first (34) and second (36) signal terminals. The common ID terminal is connected to each of the first and second signal terminals in one of four different ways: a short circuit, an open circuit, by a diode (80a) with the cathode of the diode towards the common ID terminal, and by a diode (80b) with the cathode of the diode towards the signal terminal. An oscillating signal is applied to the common terminal and to four optocouplers (54–60), which are also connected to the signal terminals, to create a four digit binary signal corresponding to the way in which the common ID and signal terminals are connected and thus corresponding to the identification of the catheter assembly.

13 Claims, 4 Drawing Sheets

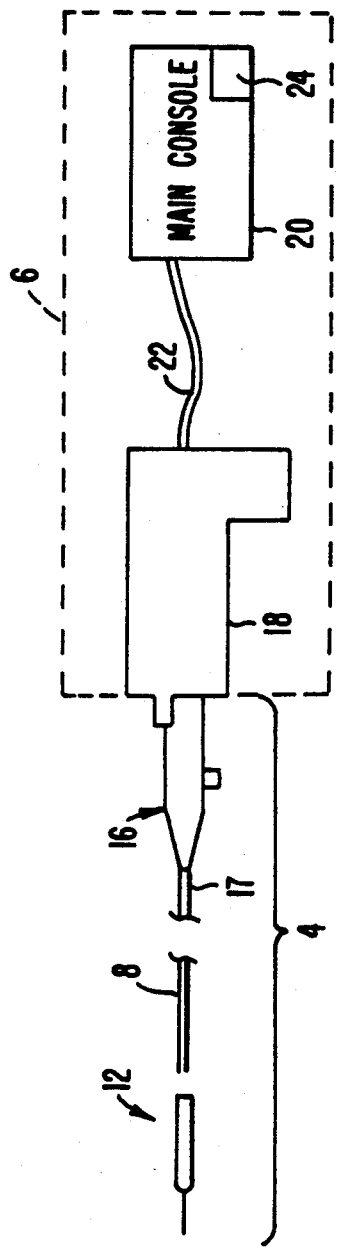
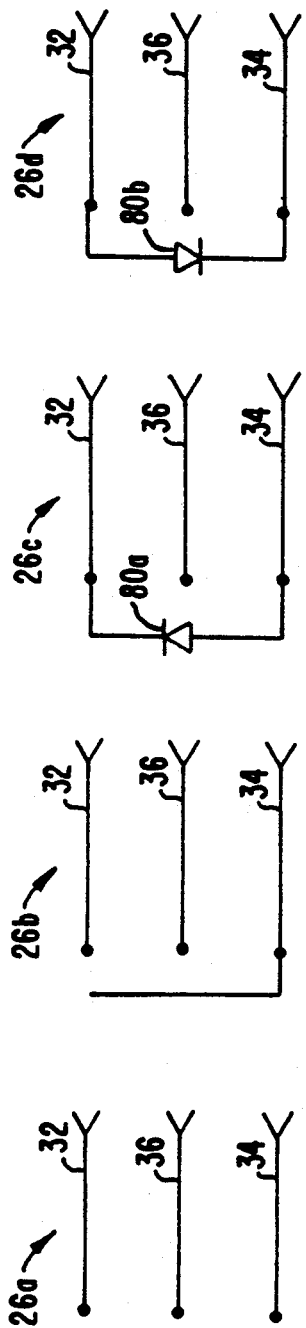
FIG. 1.
FIG. 6A.
FIG. 6B.
FIG. 6C.
FIG. 6D.

ULTRASONIC IMAGING CATHETER ASSEMBLY AND METHOD FOR IDENTIFICATION OF THE SAME

BACKGROUND OF THE INVENTION

Ultrasonic imaging catheter systems are of two major types, rotating systems and phased array systems. See U.S. Pat. No. 5,000,185, issued Mar. 19, 1991 for a description of a rotating-type catheter system, the disclosure of which is incorporated by reference. These catheter systems typically include a catheter assembly, including an elongate tubular assembly having an imaging system at the distal end and various types of connectors at the proximal end. Connectors typically have one or more ports through which irrigating liquids, acoustic coupling fluids, or fluid for expanding a balloon at the distal end can be introduced into the catheter assembly. In addition, an connector that connects to one of the catheter lumens accepts the passage of a guidewire. Various types of motor drives can be used to rotate an imaging element. Sometimes they can be used to rotate cutters or an abrasion head which can be made as a part of the imaging system. These drives are also coupled to the catheter assembly at the proximal connector. A main console, typically including a monitor, is used to display ultrasonic images and control the function of the motor drive unit and the catheter assembly.

The motor drive unit and main console, which can be referred to as a display monitor and control assembly, can be configured to be used with different types of catheter assemblies. The catheter assemblies are constructed with various dimensional configurations and transducer frequencies, and the display monitor and control apparatus must be set or initialized according to the identification of the catheter assembly. That is, what type of catheter assembly is being used must be provided to the monitor and control assembly. Heretofore, such initialization has usually been accomplished by the user inputting the necessary information to the display monitor and control assembly, typically using a keyboard, touch screen, or the like. While this is generally not difficult, it does take some time and is subject to error. Improper identification of the catheter assembly can cause erroneous information to be conveyed to the user. Although sometimes the error is evident to the operator, in some cases it may not be and may result in improper display of ultrasonic images and resulting inaccurate interpretation.

SUMMARY OF THE INVENTION

The present invention is directed to an improved ultrasonic imaging catheter assembly and a method of automatically identifying the assembly by a monitor and control assembly with which the catheter assembly is used. This permits the monitor and control assembly to automatically initialize itself according to the identification of the particular type of catheter assembly mounted to the monitor and control assembly.

The ultrasonic imaging catheter assembly is of the type including an elongate tubular assembly having an imaging system at the distal end of the tubular assembly and one or more connectors at the proximal end of the tubular assembly. The connectors are typically used to inflate balloons, direct a guidewire or direct a liquid through the elongate tubular assembly. The catheter assembly includes a digital identification circuit to permit the automatic identification of the particular type of catheter assembly by the monitor and control assembly. Usually, the digital identification circuit will be disposed within the catheter assembly itself, but it would be possible to provide the circuit in a separate adapter carrying the circuit, where the catheter can be connected to the adapter prior to connection to the remainder of the imaging system.

The digital identification circuit preferably includes a common ID terminal and at least first and second signal terminals. The common ID terminal is connected to each of the first and second signal terminals in one of four different ways: a short circuit, an open circuit, a diode with the cathode of the diode towards the common ID terminal, and the diode with the cathode of the diode towards the signal terminal.

The monitor and control assembly, in the preferred embodiment, includes an oscillator which provides an oscillating signal to the common terminal through an isolation transformer. A control assembly also includes four light emitting diodes (LEDs). The common signal line is typically connected to the cathodes of the first and third LEDs and to the anodes of the second and fourth LEDs. The first signal terminal is connected to the anode of the first LED and to the cathode of the second LED, while the second signal terminal is connected to the cathode of the third LED and to the anode of the fourth LED. In this way, the four LEDs can each assume two different (conducting and nonconducting) states to provide for up to 16 different combinations. Thus, using only a single common terminal and two signal terminals from the catheter assembly, 16 different types of catheter assemblies can be automatically identified using the LEDs and associated light sensitive devices, such as phototransistors, for accuracy and safety. Each additional signal terminal added to the catheter assembly increases the number of different digital identifications by a factor of four. Use of the LED's, together with associated light detection circuitry, provides the additional advantage that the catheter is optically isolated from the display circuitry, an important safety feature.

One of the primary advantages of the invention is that it eliminates the time, even if only a matter of seconds, it takes an operator of a catheter system to set or initialize the monitor and control assembly according to the identification of the type of catheter assembly used. Equally important, the possibility of misidentification is virtually eliminated. Reliability is further enhanced by providing the identification information in a digital format as opposed to an analog format. Safety is enhanced by optically isolating the main console and motor drive from the digital identification circuit carried by the catheter assembly, typically using LEDs and phototransistors in combination with an isolation transformer.

Other features and advantages of the invention will appear from the following description in which the preferred embodiment has been set forth in detail in conjunction with the accompanying drawings.

BRIEF DESCRIPTION OF THE DRAWINGS

FIG. 1 is a simplified overall view of a catheter system made according to the invention;

FIGS. 6A-6D illustrate the four ways in which the common ID terminal and the first signal terminal of the digital identification circuit of FIG. 2 can be connected.

DESCRIPTION OF THE PREFERRED EMBODIMENT

Figure 5:
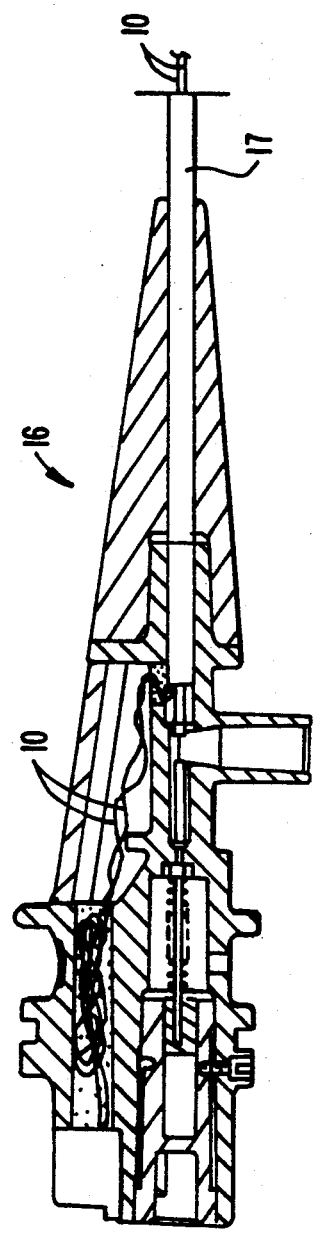
FIG. 5 is a cross-sectional view of the connector of FIG. 4.

FIG. 1 illustrates a catheter system 2 as including a catheter assembly 4 and a monitor and control assembly 6. Catheter assembly 4 includes an elongate tubular assembly 8 along which a pair of image conductor wires 10 (see FIG. 5) extend from an imaging assembly 12 at the distal end 14 of elongate tubular assembly 8 to an connector 16 at the proximal end 17 of assembly 8. Imaging assembly 12, elongate tubular assembly 8 and connector 16 are similar to corresponding elements shown in U.S. Pat. No. 5,000,185, and thus will not be described in detail.

Monitor and control assembly 6 includes a motor drive unit 18 and a main console 20 coupled to one another by a cable 22. Main console 20 includes a display 24, as is conventional, and will further include software programming and/or hard wired circuitry to decipher the catheter identification information which is provided by the circuitry and in the manner described in detail below.

Figure 2:
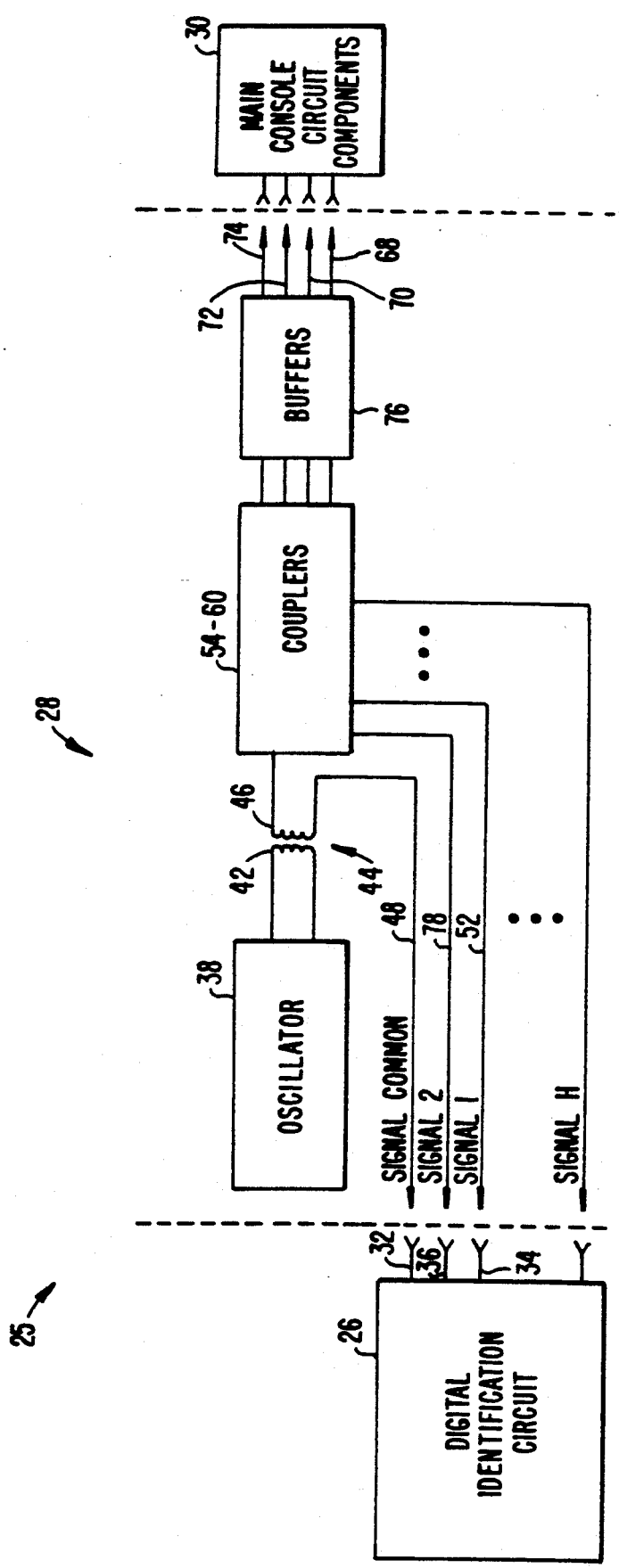
FIG. 2 is a schematic diagram of several of the catheter ID circuit components associated with the motor drive unit of FIG. 1.

FIG. 2 illustrates in schematic form the electrical components associated with identification of catheter assembly 4. Identification system 25 includes a digital identification circuit 26 carried by connector 16 of catheter assembly 4, catheter ID circuit components 28 carried, in the preferred embodiment, by motor drive unit 18, and the main console circuit components 30 carried by main console 20. As will be evident from the description of circuit 26 and circuit components 28 discussed below, the particular main console circuit components 30 used to operate on the information provided by circuit 26 and circuit components 28 are generally conventional, and need not be described in detail, but will include means (software or hardware) to decipher the digital identification information being provided by the digital identification circuit.

The digital identification circuit 26, which is resident on connector 16, includes a common ID terminal 32 and first and second signal terminals 34, 36. Common terminal 32 is connected to each of first and second signal terminals 34, 36 by one of the following: an open circuit, a short circuit, by a diode with the cathode facing common terminal 32, and by a diode with the anode facing common terminal 32. These four different states for terminals 32, 34 are illustrated in FIGS. 6A-6D. A similar set of connections can be provided between second signal terminal 36 and common ID terminal 32. Terminals 32-36 are connected in the appropriate manner according to the identification of the type of catheter assembly 4. For example, a particular type of catheter assembly 4 may have terminals 32 and 34 connected by an open circuit (that is not connected) as shown in FIG. 6A and have terminals 32 and 36 connected with a diode, the cathode of the diode facing common ID terminal 32. Using just three terminals 32-36, sixteen different combinations of connecting terminals using open circuits, short circuits and one-way circuits (using diodes) are possible. If catheter system 2 is to be used with more than sixteen different types of catheter assemblies 4, one or more additional signal terminals can be added; each signal terminal would increase the number of types of catheter assemblies which can be identified by a factor of four.

Figure 3:
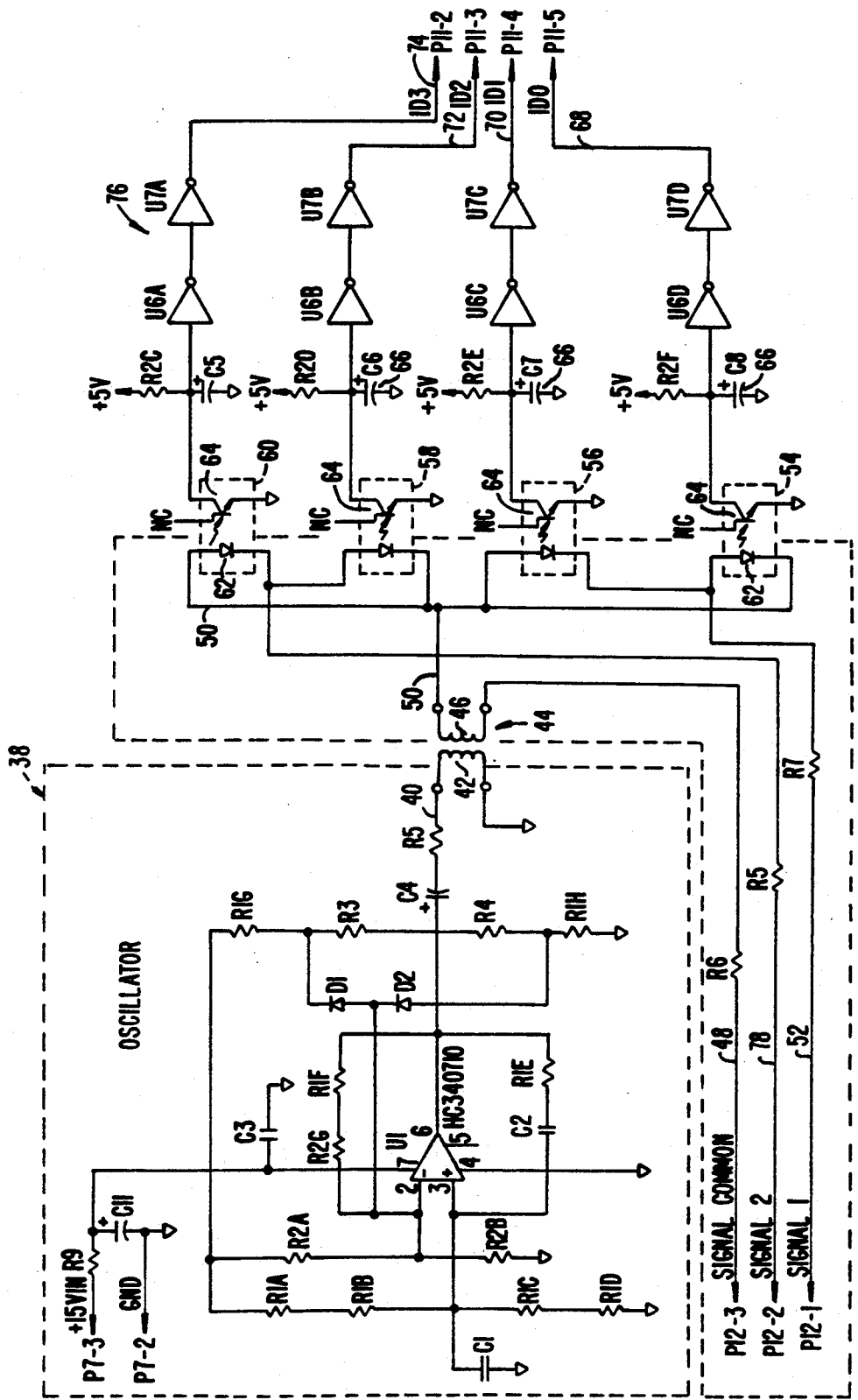
FIG. 3 is a detailed schematic diagram of the catheter ID circuit components of FIG. 2.

Referring also to FIG. 3, circuit components 28 are seen to include a generally conventional oscillator 38 having a signal line 40 connected to the primary winding 42 of a transformer 44. Transformer 44 is an important safety feature since (in combination with optocouplers 54-60, discussed below), it isolates the patient from the system electronics. Oscillator 38 provides a sinusoidal signal at a frequency of 30 KHz and peak amplitudes of ±4 volts. Other shapes, frequencies and amplitudes for the signal can also be used. Transformer 44 includes a secondary winding 46 connected to a common signal line 48 at one end and to a common line 50 at the other. Common signal line 48 is connected to common ID terminal 32 and first signal terminal 34 is connected to a first signal line 52 when motor drive unit 18 is mounted to connector 16.

Circuit components 28 include four optocouplers 54, 56, 58 and 60. Each optocoupler includes a light emitting diode (LED) 62 and a phototransistor 64. LED 62 and phototransistor 64 are positioned so that, when current passes through LED 62, light is produced and impinges upon phototransistor 64 to turn the phototransistor on and discharge its associated capacitor 66. The voltage across capacitor 66 is high or low depending upon whether the capacitor is charged or discharged so to provide digital signals (high or low) at signal terminal 68, 70, 72, 74 after having first passed through buffers 76.

Common line 50 is connected to the cathodes of LEDs 62 for optocouplers 54, 58 and to the anodes of LEDs 62 for optocouplers 56, 60. First signal line 52 is connected to the anode of LED 66 for optocoupler 54 and to the cathode of the LED for optocoupler 56. Similarly, second signal line 78 is connected to the anode of LED 62 of optocoupler 58 and the cathode of the LED 62 of optocoupler 60.

When the connection between terminals 32, 34 is in the open circuit condition of FIG. 6A, current will not pass through either LED 62 of first and second optocouplers 54, 56. Thus, the associated capacitor 56 will remain charged at about five volts so that both lines 68 and 70 will be at a logic high level. In the configuration of FIG. 6B, the oscillating signal from secondary 46 will be provided to LED 62 of first and second optocouplers 54, 56 through lines 48, 52 and 50. The photodiode 62 for first optocoupler 54 will conduct during the negative half cycle of the oscillating signal while the photodiode 62 for second optocoupler 56 will conduct during the positive half cycle of the signal. Each capacitor 66 will discharge quickly due to the low impedance of its associated phototransistor 64 when in its conducting state. During the half cycle that each phototransistor 64 is not conducting, the respective capacitor 66 will slowly recharge. However, by the appropriate sizing of the various components, the voltage across capacitor 66 will not be above about 0.1 volt before the conducting half cycle repeats to discharge the capacitors, thus keeping the logic levels low at both first and second signal terminals 68, 70.

Assuming digital identification circuit 26 is in the configuration of FIG. 6C, LED 62 for second optocoupler 56 has the same polarity as the ID diode 80a so that LED 62 of second optocoupler 56 will conduct during every half cycle as discussed above with reference to FIG. 6B so that second signal terminal 70 will be logic low. However, ID diode 80a will have the opposite polarity as LED 62 of first optocoupler 54 so that the signal will be blocked by either ID diode 80a or by LED 62 of first optocoupler 54. This will cause first signal terminal 68 to be a logic high. Finally, connecting terminals 32, 34, as shown in FIG. 6D with an ID diode 80b, will cause the opposite effect as FIG. 6C so that first signal terminal 68 will be logic low and second signal terminal 70 will be logic high.

Common ID terminal 32 and second signal terminal 36 can be connected in the same four ways illustrated with respect to FIGS. 6A–6D for first signal terminal 34. By using these various configurations, sixteen different binary codes can be provided at signal terminals 68–74 to identify catheter assembly 4 as to type. Additional signal lines, suggested in FIG. 2, will each increase the number of unique codes by a factor of four so that a common ID terminal and three signal terminals would provide 64 unique codes.

Figure 4:
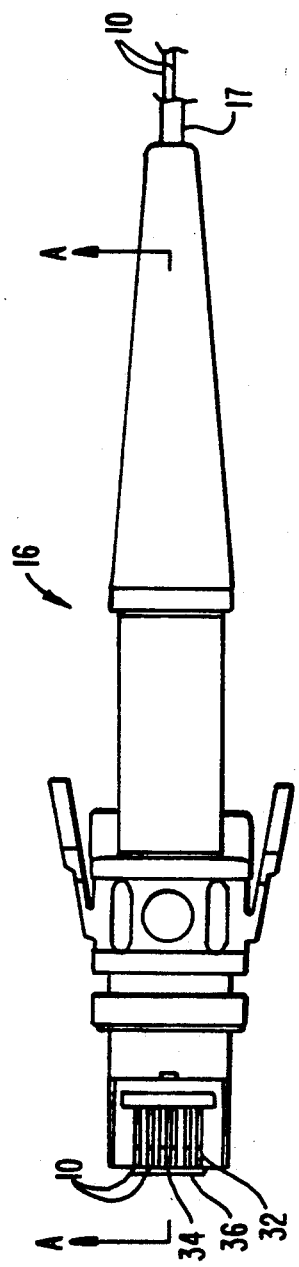
FIG. 4 is a top view of the connector at the proximal end of the catheter assembly of FIG. 1.

In use, the user simply mounts a catheter assembly 4 to motor drive unit 18 to automatically connect terminals 32–36 to corresponding terminals on the motor drive unit coupled to lines 48, 52, 78. Note that additional terminals are shown in FIG. 4 to provide electrical contacts for other information, such as that coming from imaging assembly 12 through image conduction wires 10. Main console 20 then uses the information provided at signal terminal 68–74 to virtually instantaneously identify catheter assembly 4 as to type. This digital identification information is compared to a list of known catheter assemblies found in memory. Assuming the particular catheter assembly has been identified by main console 20, the list of set points for each parameter for the particular catheter assembly 4 being used is then used in initializing monitor and control assembly 6. This is all done virtually instantaneously with very little chance of error.

The invention has been described for use with a number of different types of catheter assemblies 4. However, the invention can also be used when a number of different types of motor drive units 18 are used in addition to the different catheter assemblies. In such cases an additional digital identification circuit, similar to circuit 26, could be carried by the motor drive unit. Catheter identification circuit components 28 would typically not be carried by the motor drive unit but would be part of the main operating system, identified as main console circuit components 30 in FIG. 2. The digital identification circuit for the motor drive unit would include a common ID terminal, corresponding to terminal 32, and at least one signal terminal corresponding to signal terminals 34, 36, depending on the number of different types of motor drive units which are to be used. The circuit components corresponding to circuit components 28 could then be used to provide a digital identification signal for both the particular catheter assembly and a particular motor drive unit used.

Other modification and variation can be made to the disclosed embodiment without departing from the subject of the invention as defined in the following claims.

What is claimed is:

1. An improved ultrasonic imaging catheter assembly of the type including an elongate tubular assembly carrying an imaging assembly at the distal end of the tubular assembly, the improvement comprising:

a digital identification circuit including a plurality of ID terminals and circuit means for electrically coupling the ID terminals according to the identification of the catheter assembly, wherein the circuit includes a common ID terminal and first and second signal terminals and the circuit means further includes first means for connecting the common ID terminal to the first signal terminal and second means for connecting the common ID terminal to the second signal terminal by one of the following: a short circuit; an open circuit; a diode with the cathode of the diode towards the common ID terminal; or a diode with the cathode towards the first signal terminal, whereby the digital identification circuit can be electrically interrogated through the ID terminals to determine the identification of the catheter assembly.

2. An ultrasonic imaging catheter system comprising:
   a catheter assembly including an elongate tubular assembly, having distal and proximal ends, and an imaging assembly at the distal end; and
   means, removably coupled to the catheter assembly, for monitoring and controlling the imaging assembly;
   wherein the catheter assembly includes a digital ID circuit means for providing the monitoring and controlling means with a digital ID to identify the catheter assembly, wherein the digital ID to circuit means includes a common terminal and a first signal terminal connected by one of the following: an open circuit; a short circuit; a first ID diode with the cathode of the first ID diode towards the common terminal; or a first ID diode with the cathode of the first ID diode towards the first signal terminal.

3. The system of claim 2 wherein the catheter assembly includes first and second wires extending from the imaging assembly to the proximal end.

4. The system of claim 2 wherein the monitoring and controlling means includes first and second diodes, and means for applying an oscillating signal to a common signal line, wherein the common signal line is connected to the common terminal of the digital ID circuit and to a first terminal of said first diode and to a second terminal of said second diode, whereby the monitoring and controlling means can detect the presence of an open circuit, a short circuit, or a diode between the first signal terminal and the common terminal.

5. The system of claim 4 wherein the first signal terminal is connected to the second terminal of the first diode and to the first terminal of the second diode; whereby current is conducted through said first and second diodes in four different combinations according to how the common terminal and the first signal terminal are connected.

6. The system of claim 5 wherein the digital ID circuit means includes a second signal terminal connected to the common terminal by one of the following: an open circuit, a short circuit; a second ID diode with the cathode of the second ID diode towards the common terminal; the second ID diode with the cathode of the second ID diode towards the second signal terminal.

7. The system of claim 6 wherein the monitoring means includes third and fourth diodes and the common signal line connected to the first terminal of the third diode and to the second terminal of the fourth diode.

8. The system of claim 7 wherein the second signal terminal is connected to the second terminal of the third diode and to the first terminal of the fourth diode; whereby current is conducted through the first, second, third and fourth diodes in 16 different combinations according to how the common terminal and the first and second signal terminals are connected.

9. The system of claim 4 wherein the first terminal of the first diode is the cathode of the first diode.

10. The system of claim 2 wherein the monitoring and controlling means includes a display and means for optically coupling the digital ID circuit to the display.

11. An ultrasonic imaging catheter identification system for use with an ultrasonic imaging catheter assembly of the type including an elongate tubular assembly, having proximal and distal ends, and an imaging assembly at the distal end of the tubular assembly, the identification system comprising:

a digital identification circuit carried by the catheter assembly including a plurality of ID terminals and circuit means for electrically coupling the ID terminals according to the identification of the catheter assembly, wherein the circuit includes:
(a) a common ID terminal;
(b) first and second signal terminals;
(c) first means for connecting the common ID terminal to the first signal terminal by one of the following: a short circuit; an open circuit; a diode with the cathode of the diode towards the common ID terminal; the diode with the cathode towards the first signal terminal; and
(d) second means for connecting the common ID terminal to the second signal terminal by one of the following: a short circuit; an open circuit; a second diode with the cathode of the second diode towards the common ID terminal; the second diode with the cathode of the second diode towards the second signal terminal; and means, having output terminals and having input terminals coupleable to the ID terminals, for creating a binary signal at the output terminals corresponding to the identification of the catheter assembly.

12. The system of claim 11 wherein the binary signal creating means includes an oscillator creating an oscillatory signal at an oscillator output, first through fourth current actuated optocouplers and means for connecting the oscillator output, the ID terminals and the optocouplers.

13. A method for identifying an ultrasonic imaging catheter assembly by type comprising the following steps:

providing a catheter assembly with a digital ID circuit having at least first and second terminals, the first and second terminals connected by one of the following: an open circuit; a short circuit; a first ID diode with the cathode of the first ID diode towards the first terminal; the first ID diode with the cathode of the first ID diode towards the second terminal;

applying an oscillating signal to the first terminal;

coupling the first and second terminals to a digital sensing circuit having first and second digital outputs, the digital sensing circuit providing four different digital signal combinations at the digital outputs according to how the first and second terminals are connected; and monitoring the digital signals of at least the first and second digital outputs to identify the ultrasonic imaging catheter.

* * * * *